United States Patent [19]

Omatsu et al.

[11] Patent Number: 5,434,311
[45] Date of Patent: Jul. 18, 1995

[54] RHODIUM-CONTAINING CATALYST

[75] Inventors: Toshihiro Omatsu; Yasuo Tokitoh, both of Ibaragi, Japan

[73] Assignee: Kuraray Co., Ltd., Kurashiki, Japan

[21] Appl. No.: 229,676

[22] Filed: Apr. 19, 1994

[30] Foreign Application Priority Data

Apr. 19, 1993 [JP] Japan .................................. 5-115316
May 7, 1993 [JP] Japan .................................. 5-131376

[51] Int. Cl.$^6$ .............................................. C07C 45/50
[52] U.S. Cl. .................................... 568/454; 568/448; 568/451
[58] Field of Search ......................... 568/454, 451, 448

[56] References Cited

U.S. PATENT DOCUMENTS

| | | | |
|---|---|---|---|
| 4,238,419 | 12/1980 | Matsumoto et al. | 568/454 |
| 4,420,640 | 12/1983 | Matsumoto et al. | 568/454 |
| 4,510,332 | 4/1985 | Matsumoto et al. | 568/454 |
| 4,595,753 | 6/1986 | Oswald et al. | 546/2 |
| 4,663,468 | 5/1987 | Tokitoh et al. | 549/273 |
| 4,808,737 | 2/1989 | Yoshimura et al. | 549/423 |
| 4,861,922 | 8/1989 | Tokitoh et al. | 568/865 |
| 4,871,880 | 10/1989 | Omatsu et al. | 568/454 |

FOREIGN PATENT DOCUMENTS

| | | |
|---|---|---|
| 0104375 | 4/1984 | European Pat. Off. . |
| 0151282 | 8/1985 | European Pat. Off. . |
| 0158518 | 10/1985 | European Pat. Off. . |
| 0287066 | 10/1988 | European Pat. Off. . |
| 2314910 | 1/1977 | France . |
| 1592536 | 7/1981 | United Kingdom . |

*Primary Examiner*—Werren B. Lone
*Attorney, Agent, or Firm*—Oblon, Spivak, McClelland, Maier, & Neustadt

[57] ABSTRACT

In hydroformylation comprising allowing an ethylenically unsaturated compound to react with carbon monoxide and hydrogen in the presence of a catalyst to convert it into a corresponding aldehyde, the catalyst is a rhodium-containing catalyst comprising;

(a) a rhodium compound;
(b) an organic phosphorus compound having at least one tertiary amine residual group and at least one tertiary phosphorus residual group, having the ability of coordination to said rhodium compound; and optionally
(c) an acidic compound with which at least part of the tertiary amine residual group of the organic phosphorus compound is converted into ammonium ions.

20 Claims, No Drawings

RHODIUM-CONTAINING CATALYST

BACKGROUND OF THE INVENTION

1. Field of the Invention

This invention relates to a rhodium-containing catalyst especially suited as a hydroformylating catalyst used when a corresponding aldehyde is produced by subjecting an ethylenically unsaturated compound, carbon monoxide and hydrogen to the reaction of hydroformylation. This invention also relates to a process for reversibly ionizing or nonionizing such a catalyst, which makes it possible to recycle the catalyst, and a hydroformylation process that utilizes such reversible ionization or nonionization.

The present invention is also concerned with a process for producing an aldehyde by the use of the rhodium-containing catalyst, and a process for recovering the hydroformylating catalyst from a hydroformylation reaction mixture.

2. Related Art of the Invention

The reaction of converting an ethylenically unsaturated compound into an aldehyde by allowing it to react with carbon monoxide and hydrogen in the presence of a catalyst is called hydroformylation or oxo synthesis. It is industrially very highly valuable to utilize this reaction for the production of aldehydes.

Catalysts used in such hydroformylation commonly include cobalt compounds and rhodium compounds. In view of their catalytic activities and their properties of selective formation of aldehydes, the latter rhodium compounds are known to be superior to the former cobalt compounds.

Such rhodium compounds can be exemplified by rhodium salts such as rhodium oxide and rhodium complexes such as rhodium carbonyl. These may be used alone. In order to improve stability of these compounds or improve their catalytic activities, however, they are rather used in the form of complexes modified with ligands such as organic phosphorus compounds, organic arsenic compounds or organic antimony compounds.

Among these ligands, organic phosphorus compounds are preferably used in view of their toxicity and production cost. Of the organic phosphorus compounds, the state in which a phosphorus atom is bonded or the types of substituents bonded to the phosphorus atom are selected properly according to the types of the starting material ethylenically unsaturated compounds and those of desired aldehydes. More specifically, compounds such as tertiary phosphines or phosphites, the number of phosphorus atoms that indicates whether the ligands are unidentate, bidentate or higher and the type of substituents that indicates whether the ligands are alkyl-substituted or phenyl-substituted are used properly in appropriate geometry.

As examples in which organic phosphorus compounds are used as the ligands of hydroformylating catalysts comprised of a rhodium compound, the following are proposed.

(A) When straight-chain aldehydes are selectively produced, a rhodium compound is modified with a tertiary phosphine (Japanese Patent Publication No. 45-10730);

(B) when branched-chain or straight-chain aldehydes are selectively produced from olefins having a functional group, such as methyl methacrylate or allyl alcohol, a rhodium compound is modified with a bidendate tertiary phosphine (Bull. Chem. Soc. Jpn., 50, 2351, 1977; Japanese Patent Application Laid-open No. 54-106405); and (C) in order to increase the reaction rate when aldehydes are produced from branched olefins having a great static hindrance, such as 3-methyl-3-buten-1-ol, a rhodium compound is modified with a triphenyl phosphite substituted with an alkyl group at the 2-position of a phenyl group thereof (Japanese Patent Application Laid-open No. 62-201881).

Incidentally, rhodium compounds are very expensive and hence, when they are used as hydroformylating catalysts in an industrial scale, it becomes necessary to recover them so that they can be recycled. For this purpose, as methods for recovering usual hydroformylating catalysts, including the hydroformylating catalysts proposed in the prior art as stated in the above (A) to (C), it has been common to recover hydroformylating catalysts by heating a reaction mixture formed after hydroformylation, separating reaction products and unreacted reaction materials from the reaction mixture by distillation and then collecting the hydroformylating catalysts as distillation residues.

When, however, hydroformylating catalysts are recovered in this way, there has been the problem that the catalysts may deteriorate to have a short lifetime because of the heating carried out when the reaction products are distilled from the reaction mixtures. In particular, in instances in which the reaction products have a high boiling point, the lifetime of the catalysts becomes very short. Moreover, because of such heating, the reaction product may undergo decomposition or condensation to form catalyst poisons, or compounds with a high boiling point may accumulate, bringing about the problem that it becomes impossible to recycle the catalysts.

To solve such problems, it is proposed, when aliphatic olefins having 2 to 12 carbon atoms are hydroformylated, to use a rhodium catalyst with a ligand comprising a sulfonated or carboxylated water-soluble triarylphosphine to carry out hydroformylation in an aqueous phase, followed by separation of the product from the catalyst by decantation (Japanese Patent Application Laid-open No. 60-228439). It is also proposed to use a water-soluble binuclear complex as a hydroformylating catalyst (Japanese Patent Application Laid-open No. 61-97295).

It is still also proposed to carry out hydroformylation in the presence of a non-aqueous polar solvent, using an ionic metal complex catalyst with a ligand comprising a water-soluble organic phosphorus compound having a trisulfonated salt residual group, followed by extraction of the product from the reaction mixture by the use of a hydrocarbon solvent to recover the catalyst in the form of a solution of the non-aqueous polar solvent (Japanese Patent Application Laid-open No. 62-145038).

It is further proposed to carry out hydroformylation in the presence of a non-aqueous polar solvent, using an ionic metal complex catalyst with a ligand comprising a water-soluble organic phosphorus compound having a monosulfonated salt residual group, followed by extraction of the product from the reaction mixture by the use of water as an extracting reagent to recover the catalyst from the reaction mixture in the form of an aqueous solution (EP0350,922).

However, the methods disclosed in the foregoing Japanese Patent Applications Laid-open No. 60-228439 and No. 61-97295 have the problem that the starting material olefin has so low a solubility in the aqueous phase that no hydroformylation can be carried out at a reaction rate that can be satisfactory from an industrial aspect.

The method disclosed in Japanese Patent Application Laid-open No. 62-145038 is involved in the problem that the phosphorus compound as a ligand, having a trisulfonated salt residual group, is so hard to dissolve in usual hydrocarbon olefins that the non-aqueous polar solvent must be used in a large quantity. In addition, even when the non-aqueous polar solvent is used in a large quantity, the organic phosphorus compound can have no satisfactory solubility in such a solvent, and hence the molar ratio of phosphorus to rhodium can not be made higher, to cause the problem of a difficulty in selective production of straight-chain aldehydes.

In the method disclosed in EP0350,922, the organic phosphorus compound as a ligand, having a monosulfonated salt residual group, is so hard to dissolve in usual olefins that the non-aqueous polar solvent must be used. In addition, the organic phosphorus compound has no satisfactory solubility in such a non-aqueous polar solvent. Hence, there is the problem that, in order to make the molar ratio of phosphorus to rhodium higher, the non-aqueous polar solvent must be used in such a large quantity that may cause an apparent decrease in productivity.

Besides the problems discussed above, there is the problem that, in an attempt to hydroformylate unsaturated aliphatic hydrocarbons not miscible with non-aqueous polar solvents such as dimethyl sulfoxide as in the case of octenes, the organic phosphorus compounds as described above can not substantially dissolve in the starting material unsaturated aliphatic hydrocarbons, so that the hydroformylation does not proceed at a reaction rate that can be satisfactory from an industrial aspect. Hence, there is also the problem that the unsaturated aliphatic hydrocarbons to which the methods disclosed in the above publications can be applied are in a very limited scope.

As discussed above, in the prior art methods, the polar phosphorus ligands that are originally hard to dissolve in nonpolar materials and nonpolar reaction products are barely dissolved therein by the use of the polar solvents, necessarily bringing about a limit in the amount of each component used.

The hydroformylation in the prior art described above is also industrially limited to instances in which starting materials and reaction products contain no inorganic salt residual group. Hence, there is the problem that the hydroformylation can not be applied to instances in which corresponding aldehydes are produced from ethylenically unsaturated compounds having an inorganic salt residual group, because of a great difficulty in the recycling of catalysts. This is because almost all of the ethylenically unsaturated compounds having an inorganic salt residual group and their hydroformylation products (i.e., aldehydes) are solid and hence it is substantially impossible to separate these and catalysts by distillation. As additional reasons stated below, it is also substantially impossible to separate them by extraction.

That is, the ethylenically unsaturated compounds having an inorganic salt residual group can only dissolve in polar solvents such as water and methanol, and hence phosphorus ligands or the like substituted with a polar group such as a sulfonate residual group can only be used as the ligands of hydroformylating catalysts used in the hydroformylation of such ethylenically unsaturated compounds. In such an instance, if polar solutions mainly composed of water or methanol are used so that such hydroformylating catalysts to the metal rhodium of which phosphorus ligands are coordinated can be recovered by extraction, both the catalysts and the reaction products are extracted since the hydroformylation products are water-soluble, and can not be separated.

Meanwhile, one may contemplate using nonpolar phosphorus ligands in order to make it possible to extract catalysts from reaction mixtures containing water-soluble hydroformylation products. However, such nonpolar phosphorus ligands have the problem that, in the solution mainly composed of water or methanol that serves as a reaction solution in such an instance, they can not be dissolved to an extent large enough to carry out the hydroformylation in an industrial scale.

SUMMARY OF THE INVENTION

Objects of the present invention are to solve the problems involved in the prior art discussed above, and to make it possible to carry out hydroformylation of an ethylenically unsaturated compound to produce an aldehyde, without using non-aqueous polar solvents in a large quantity, at an industrially satisfactory reaction rate and preferably without regard to the polarity of the ethylenically unsaturated compound, to recover catalysts with ease in a high yield, and to recycle the catalysts thus recovered.

The present inventors have discovered that the above objects can be achieved by the following.

When an ethylenically unsaturated compound, carbon monoxide and hydrogen are allowed to react, a hydroformylating catalyst should be dissolved in a reaction solution so that only the catalyst can be extracted after the reaction has been completed. For that purpose, the catalyst should be made to have different polarities at the time of reaction and at the time of extraction, and accordingly the catalyst should be made to have polarities reversibly convertible. In order to make the catalyst have the polarities thus convertible, the ligand of a rhodium compound should be made to have such a function. In order for the ligand to accomplish such a function, an organic phosphorus compound having at least one tertiary amine residual group should be used as the ligand so that the tertiary amine residual group is formed into ammonium ions by using carbon dioxide gas and water or becomes nonionized by releasing the carbon dioxide gas.

We have also discovered that the above objects can be achieved when an organic phosphorus compound water-soluble and capable of dissolving also in unsaturated aliphatic hydrocarbons is used as a ligand of the rhodium compound. For such purpose, in the organic phosphorus compound at least one tertiary amine residual group should be present, where the tertiary amine residual group should be formed into ammonium ions and also at least one tertiary phosphorus residual group should be present.

In a first mode, the present invention provides a rhodium-containing catalyst comprising;

(a) a rhodium compound; and (b) an organic phosphorus compound having at least one tertiary amine residual group and at least one tertiary phosphorus residual group, having the ability of coordination to said rhodium compound.

In a second mode, the present invention provides a process of reversibly ionizing the rhodium-containing catalyst of the first mode, which is a process of reversibly ionizing a rhodium-containing catalyst, comprising the step of bringing said catalyst into contact with water and carbon dioxide gas to cause them to react so that a tertiary amine residual group of said organic phosphorus compound is formed into an ammonium carbonate to ionize said catalyst.

In a third mode, the present invention provides a process of reversibly nonionizing the rhodium-containing catalyst having been reversibly ionized by the process described above, which is a process of reversibly nonionizing a rhodium-containing catalyst, comprising the step of releasing carbon dioxide gas from an ionized catalyst to nonionize said ionized catalyst.

In a fourth mode, the present invention provides a process of hydroformylation comprising allowing a water-insoluble ethylenically unsaturated compound to react with carbon monoxide and hydrogen in the presence of the above rhodium-containing catalyst to produce an aldehyde, wherein the process comprises the steps of ionizing a catalyst in a reaction mixture by the above process of reversible ionization so that the catalyst can be separated from a water-insoluble hydroformylation product after the reaction, subsequently transferring the ionized catalyst to an aqueous layer by extraction, further nonionizing the catalyst contained in the aqueous layer by the above process of reversible nonionization, and transferring the nonionized catalyst to a water-insoluble organic medium by extraction.

In a fifth mode, the present invention provides a process of hydroformylation comprising allowing a water-soluble ethylenically unsaturated compound to react with carbon monoxide and hydrogen in the presence of the above rhodium-containing catalyst ionized by the above process of reversible ionization, to produce an aldehyde, wherein the process comprises the steps of nonionizing a catalyst ionized in a resulting reaction mixture, by the above process of reversible nonionization so that the catalyst can be separated from a water-soluble hydroformylation product after the reaction, and transferring the nonionized catalyst to a water-insoluble organic medium by extraction.

In a sixth mode, the present invention provides a rhodium-containing catalyst comprising;
(a) a rhodium compound;
(b) an organic phosphorus compound having at least one tertiary amine residual group and at least one tertiary phosphorus residual group, having the ability of coordination to said rhodium compound; and
(c) an acidic compound with which at least part of the tertiary amine residual group of the organic phosphorus compound is converted into ammonium ions.

In a seventh mode, the present invention provides a process for producing an aldehyde, comprising the step of allowing an ethylenically unsaturated compound to react with carbon monoxide and hydrogen in the presence of a catalyst to carry out hydroformylation to obtain a reaction mixture containing a corresponding aldehyde, wherein the rhodium-containing catalyst described above is used as the catalyst.

In an eighth mode, the present invention provides a process for recovering a rhodium-containing catalyst from a reaction mixture obtained by the above process for producing an aldehyde, wherein the reaction mixture is brought into contact with water so that the rhodium-containing catalyst is transferred to an aqueous layer by extraction, and the water is removed from the resulting aqueous extract.

DETAILED DESCRIPTION OF THE INVENTION

The present invention will be described below in detail.

The rhodium compound used in the first mode of the present invention is a compound originally having a catalytic action that accelerates the hydroformylation of an ethylenically unsaturated compound, or capable of gaining such a catalytic action under conditions for the hydroformylation. Any rhodium compounds conventionally used in hydroformylating catalysts can be used. Such rhodium compounds can be exemplified by rhodium oxides such as RhO, $Rh_2O$, $Rh_2O_3$ and $RhO_2$, rhodium salts or halides such as rhodium nitrate, rhodium sulfate, rhodium chloride, rhodium iodide and rhodium acetate, and rhodium complexes such as $Rh_4(CO)_{12}$, $Rh_6(CO)_{16}$, $Rh(acac)(CO)_2$ and rhodium acetylacetonate.

In the present invention, an organic phosphorus compound having at least one tertiary amine residual group and at least one tertiary phosphorus residual group, having the ability of coordination to the rhodium compound is used as a ligand of the rhodium compound.

This organic phosphorus compound is formed into ammonium carbonate and becomes ionized after its tertiary amine residual group has reacted with water and carbon dioxide gas. Thus, the catalyst itself to the metal rhodium of which the ligand organic phosphorus compound(s) is/are coordinated is also ionized to become water-soluble. It therefore becomes possible to extract the catalyst with water or to carry out hydroformylation in an aqueous phase.

As for the ammonium carbonate residual group in the ionized catalyst, it becomes nonionized upon release of the carbon dioxide gas by heating or the like, and returns to the original tertiary amine residual group. Thus, the catalyst itself is also nonionized to become water-insoluble. It therefore becomes possible to transfer the catalyst to a non-aqueous organic medium by extraction or to carry out hydroformylation in a nonaqueous organic phase.

In this way, using as the ligand of a rhodium compound the organic phosphorus compound having at least one tertiary amine residual group and at least one tertiary phosphorus residual group, the catalyst can be reversibly ionized or nonionized. Thus, when the hydroformylation is carried out, the catalyst can be present in the same phase as starting materials and reaction products are present and can be separated to a phase different from that of the starting materials and reaction product.

There are no particular limitations on the organic phosphorus compound having at least one tertiary amine residual group and at least one tertiary phosphorus residual group, so long as it can act as described above. The tertiary amine residual group can be exemplified by those in which three alkyl groups or aryl groups are bonded to the N atom. The tertiary phosphorus residual group may have the structure of a phosphine, a phosphite or the like. Such organic phosphorus compounds, preferably usable, may include compounds represented by any of the following Formulas (1) to (4).

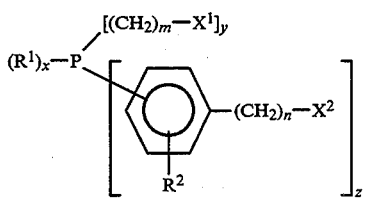

Formula (1)

In Formula (1), $R^1$ represents a hydrocarbon groups having 1 to 10 carbon atoms, such as a straight-chain, branched or cyclic alkyl group, a phenyl group or a naphthyl group, any of which may be optionally substituted with other substituent such as a hydroxyl group or a halogen atom; $R^2$ represents a hydrogen atom, an alkyl group having 1 to 5 carbon atoms, such as methyl, ethyl, isopropyl or cyclopentyl, a nitro group, or a halogen atom such as chlorine or bromine; m is 1, 2 or 3, and n is 0 or 1; x is 0, 1 or 2, and y and z are each independently 0, 1, 2 or 3, provided that the sum of x, y and z is 3; and $X^1$ and $X^2$ each independently represent a hydrogen atom or $-NR^3R^4$, where $R^3$ and $R^4$ each independently represent an alkyl group having 1 to 4 carbon atoms, such as methyl, ethyl, propyl, isopropyl or butyl, provided that $X^1$ and $X^2$ are not hydrogen atoms at the same time when both y and z are not 0, $X^2$ is $-NR^3R^4$ when y is 0, and $X^1$ is $-NR^3R^4$ when z is 0.

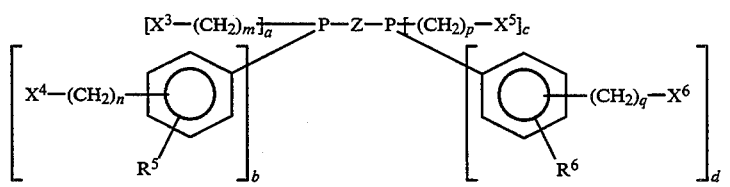

Formula (2)

In Formula (2), $R^5$ and $R^6$ each independently represent a hydrogen atom, an alkyl group having 1 to 5 carbon atoms, such as methyl, ethyl, isopropyl or cyclopentyl, a nitro group, or a halogen atom such as chlorine or bromine; m and n are as defined in Formula (1), p is 1, 2 or 3, and q is 0 or 1; a, b, c and d are each independently 0, 1 or 2, provided that the sum of a, b, c and d is 4; Z represents a divalent hydrocarbon group having 1 to 10 carbon atoms, such as methylene, ethylene or cyclohexylene; and $X^3$, $X^4$, $X^5$ and $X^6$ each independently represent a hydrogen atom or $-NR^3R^4$ where $R^3$ and $R^4$ are as defined in Formula (1), provided that $X^3$, $X^4$, $X^5$ and $X^6$ are not hydrogen atoms at the same time when a, b, c and d are each 1, at least one of $X^4$, $X^5$ and $X^6$ is $-NR^3R^4$ when a is 0, at least one of $X^3$, $X^5$ and $X^6$ is $-NR^3R^4$ when b is 0, at least one of $X^3$, $X^4$ and $X^6$ is $-NR^3R^4$ when c is 0 and at least one of $X^3$, $X^4$ and $X^5$ is $-NR^3R^4$ when d is 0.

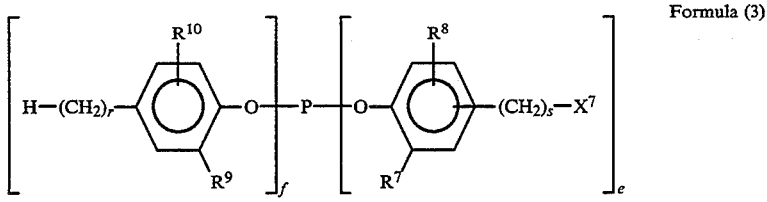

Formula (3)

In Formula (3), $R^7$ and $R^9$ each independently represent a hydrogen atom, an alkyl group having 1 to 6 carbon atoms, such as methyl, ethyl or isopropyl, or a phenyl group; $R^8$ and $R^{10}$ each independently represent a hydrogen atom, an alkyl group having 1 to 6 carbon atoms, such as methyl, ethyl or isopropyl, a nitro group, or a halogen atom such as chlorine or bromine; r and s are each independently 0, 1, 2 or 3; e is 1, 2 or 3; and f is 0, 1 or 2, provided that the sum of e and f is 3; and $X^7$ represents $-NR^3R^4$ where $R^3$ and $R^4$ are as defined in Formula (1).

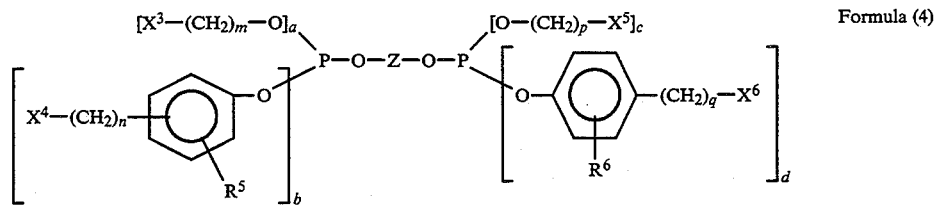

Formula (4)

In Formula (4), $R^5$, $R^6$, m, n, p, q, a, b, c, d, $X^3$, $X^4$, $X^5$, $X^6$ and Z are as defined in Formula (2).

Of these compounds of Formulas (1) to (4), more preferable specific organic phosphorus compounds can be exemplified by the following formulas (5) to (22)

| | |
|---|---|
| $P[CH_2N(C_2H_5)_2]_3$ | (5) |
| $(C_4H_9)_2PCH_2N(CH_3)_2$ | (6) |
| $(C_4H_9)_2PCH_2CH_2N(CH_3)_2$ | (7) |
| $P[CH_2CH_2CH_2N(CH_3)_2]_3$ | (8) |
| $P[CH_2CH_2CH_2N(C_2H_5)_2]_3$ | (9) |
| $P[CH_2CH_2N(t-C_4H_9)_2]_3$ | (10) |
| $(C_8H_{17})P[CH_2N(CH_3)_2]_2$ | (11) |
| $(C_6H_{13})_2PCH_2CH_2CH_2N(CH_3)_2$ | (12) |

$(C_6H_5)_2PCH_2N(CH_3)_2$ (13)

$(C_6H_5)_2PCH_2CH_2N(CH_3)_2$ (14)

$P[CH_2CH_2C_6H_4N(CH_3)_2]_3$ (15)

$P[C_6H_4N(CH_3)_2]_3$ (16)

$P[C_6H_4CH_2N(CH_3)_2]_3$ (17)

$C_6H_5P[C_6H_4N(CH_3)_2]_2$ (18)

$C_6H_5P[C_6H_4CH_2N(CH_3)_2]_2$ (19)

$C_6H_5P[CH_2CH_2CH_2N(CH_3)_2]_2$ (20)

$(C_6H_5)_2P[C_6H_4N(CH_3)_2]$ (21)

$(C_6H_5)_2P[C_6H_4CH_2N(i-C_3H_7)_2]$ (22)

In the rhodium-containing catalyst according to the first mode of the present invention, use of the organic phosphorus compound in an excessively small amount may damage the stability of the catalyst, and its use in an excessively large amount may result in a decrease in reaction rate. Hence, the component-(b) organic phosphorus compound may preferably be used in a gram atomic weight of from 1 to 10,000 g, and more preferably from 10 to 1,000 g, in terms of phosphorus atoms, based on 1 gram atom of the component-(a) rhodium compound in terms Of rhodium atoms.

In the present invention, when the component-(b) organic phosphorus compound is used in excess with respect to the component-(a) rhodium compound, it follows that any organic phosphorus compound(s) not serving as the ligand(s) coordinated to the centeral metal of the rhodium compound is/are also present. Such organic phosphorus compound(s) not serving as the ligand(s) coordinated to the centeral metal of the rhodium compound may preferably be made present in the same phase as the rhodium-containing catalyst so that the reaction conditions for hydroformylation can be kept as constant as possible when the catalyst is recycled. For this purpose, the organic phosphorus compound(s) not serving as the ligand(s) coordinated to the centeral metal of the rhodium compound may preferably be reversibly ionized or nonionized in the same manner as the ligand organic phosphorus compound(s) coordinated to the centeral metal of the rhodium compound.

In the process of reversible ionization according to the second mode of the present invention, the catalyst having such components is allowed to react with water and carbon dioxide gas so that the tertiary amine residual group of the ligand organic phosphorus compound is converted into ammonium carbonate to ionize the catalyst. In this case, an excessively high reaction temperature may cause the rate of release of carbon dioxide gas to become higher than the rate of ionization. On the other hand, an excessively low reaction temperature may cause the rate of ionization to become excessively low. Hence, the reaction may preferably be carried out at a temperature ranging from 10° to 50° C. There are no particular limitations on the pressure of carbon dioxide gas. In view of operability, the reaction may preferably be carried out at a pressure ranging from 1 to 50 arm.

In the process of reversible nonionization according to the third mode of the present invention, the catalyst thus ionized is reversibly nonionized by releasing carbon dioxide gas by a known method, from the tertiary amine residual group converted into the ammonium carbonate which is the ligand of its organic phosphorus compound. For example, the catalyst having been ionized may be heated at 70° to 100° C. in an aqueous phase or the catalyst may be made to stand under reduced pressure, so that it becomes nonionized.

The process of hydroformylation for producing an aldehyde by allowing an ethylenically unsaturated compound to react with carbon monoxide and hydrogen in the presence of the above rhodium-containing catalyst that can be reversibly ionized or nonionized will be described below in detail by dividing it into 1) an instance (the fourth mode) where the ethylenically unsaturated compound and the corresponding reaction product are water-insoluble (i.e., non-polar) and 2) an instance (the fifth mode) where the ethylenically unsaturated compound and the corresponding reaction product are water-soluble (i.e., polar).

1) Instance where the ethylenically unsaturated compound and the corresponding reaction product are water-insoluble (i.e., non-polar):

1-a)

First, a water-insoluble ethylenically unsaturated compound is converted into a corresponding aldehyde by allowing it to react with carbon monoxide and hydrogen to effect hydroformylation, in the presence of the rhodium-containing catalyst comprised of the above component-(a) rhodium compound and component-(b) organic phosphorus compound, having been not ionized. Stated specifically, the water-insoluble ethylenically unsaturated compound and the rhodium-containing catalyst are charged into a reactor such as a stirred tank reactor or a bubble column reactor, and a mixed reaction gas of hydrogen and carbon monoxide ($H_2/CO$, preferably in a molar ratio of about 0.5 to 5) is fed into this reactor at a pressure of usually from 1 to 300 arm, and preferably from 5 to 100 arm, followed by heating at usually from 20° to 160° C., and preferably from 50° to 140° C., with stirring. In this case, the rhodium-containing catalyst may preferably be prepared by separately introducing the component-(a) and the component-(b) into the hydroformylation reaction system, and allowing the both to react in that system to form a complex. Such reaction may also be carried out by a continuous method or a batch method.

Use of the rhodium-containing catalyst in an excessively small amount in the hydroformylation may make the reaction rate excessively low, and on the other hand its use in an excessively large amount can not make the reaction rate effectively high, rather resulting in an excessive increase in the cost of the catalyst. Hence, it may preferably be in a concentration of a milligram atomic weight ranging from 0.001 to 10 mg, and more preferably from 0.005 to 5 mg, in terms of rhodium atoms, per liter of the reaction solution.

In the case of a unidentate compound, the organic phosphorus compound in the reaction solution may preferably be in a concentration, which may vary depending on the type of the rhodium compound, of a milligram atomic weight ranging from 0.1 to 500 mg, and more preferably a milligram atomic weight ranging from 0.5 to 200 mg, in terms of phosphorus atoms, per liter of the reaction solution. In the case of a bidentate or higher organic phosphorus compound, the compound may preferably be used in an amount ranging from 0.1- to 5-fold mols based on the rhodium atoms.

In this hydroformylation, an inert water-insoluble organic solvent may be used. For example, aromatic compounds such as benzene, toluene and xylene, aliphatic hydrocarbons such as hexane, octane and cyclohexane, ethers such as diethyl ether and diphenyl ether, ketones such as cyclohexanone and methyl isobutyl ketone, and esters such as dioctyl phthalate and ethyl acetate may be used under appropriate selection.

1-b)

Next, the rhodium-containing catalyst in the hydroformylation reaction mixture is allowed to react with carbon dioxide gas in the presence of water by the above process of reversible ionization according to the second mode of the present invention, to ionize it (make it polar), and the resulting ionized catalyst is transferred by extraction, to an aqueous medium serving as an extracting reagent. This enables separation of the water-insoluble reaction product and the catalyst with ease, and enables separation of the reaction product and recovery of the catalyst with ease. The recovery of the catalyst by means of extraction also makes the catalyst free from being heated together with the reaction product when the reaction product is separated, so that the catalyst can be avoided from deteriorating by heat, or from being poisoned by heat because of the reaction product or its decomposition product, making it possible to elongate the lifetime of the catalyst.

As the aqueous medium, water may preferably be used, which may be used in an amount of from 1/10 to 10/1 times by volume, and preferably from 1/5 to 5/1 times by volume of the reaction mixture.

In order to accelerate the layer separation, it is also possible to add aromatic hydrocarbons such as benzene and toluene, or aliphatic hydrocarbons such as hexane and cyclohexane.

In order to prevent deterioration of the catalyst, the extraction in the aqueous medium may preferably be operated under carbon dioxide gas pressure (preferably at a pressure of 1 to 50 arm) at a temperature of from 10 to 50° C.

1-c)

Next, the carbon dioxide gas is released from the catalyst contained in the aqueous layer by the above process of reversible nonionization according to the third mode of the present invention, to nonionize the catalyst (make it nonpolar), and the resulting catalyst is transferred to a water-insoluble organic medium by extraction. At this time, using the starting material water-insoluble ethylenically unsaturated compound as the water-insoluble organic medium, it becomes possible to again simply carry out the hydroformylation, so that the recycling of the catalyst can be achieved with ease.

The water-insoluble organic medium may be used in an amount of from 1/10 to 10/1 times by volume, and preferably from 1/5 to 5/1 times by volume of the reaction mixture. In order to accelerate the release of carbon dioxide gas, the nonionization of the catalyst and the extraction with the water-insoluble organic medium may preferably be carried out at a temperature of from 70° to 110° C. These may also be carried out under reduced pressure.

The hydroformylation product (an aldehyde) thus separated can be isolated by usual means such as crystallization or distillation.

2) Instance where the ethylenically unsaturated compound and the corresponding reaction product are water-soluble (i.e., polar):

2-a)

First, a water-soluble ethylenically unsaturated compound is converted into a corresponding aldehyde by allowing it to react with carbon monoxide and hydrogen to effect hydroformylation, in the presence of the rhodium-containing catalyst comprised of the above component-(a) rhodium compound and component-(b) organic phosphorus compound, having been ionized by the process of reversible ionization according to the second mode of the present invention. Stated specifically, the water-soluble ethylenically unsaturated compound, the rhodium-containing catalyst having been not ionized and water are charged into a reactor such as a stirred tank reactor or a bubble column reactor, and carbon dioxide gas is fed into this reactor to ionize the catalyst, followed by feeding of a mixed reaction gas of hydrogen and carbon monoxide. In this case, the hydroformylation may be carried out under the conditions as described in the hydroformylation of the water-insoluble ethylenically unsaturated compound. However, as the solvent used, it is possible to use not water-insoluble ones but water-soluble organic solvents such as dimethyl sulfoxide, sulfolane, lower alcohols and acetone.

In order to prevent the catalyst from becoming nonionized in the course of the hydroformylation, the partial pressure of carbon dioxide gas in the gaseous phase should preferably be kept at a pressure of from 0.1 arm to 100 arm.

2-b)

Next, the carbon dioxide gas is released from the catalyst contained in the hydroformylation reaction mixture by the above process of reversible nonionization according to the third mode of the present invention, to nonionize the catalyst, and the resulting catalyst is transferred to a water-insoluble organic medium by extraction. The nonionization of the catalyst and the extraction thereof may be operated in parallel at the same time.

Such extraction enables separation of the water-soluble hydroformylation product and the catalyst with ease, and enables separation of the reaction product and recovery of the catalyst with ease. The recovery of the catalyst by means of extraction also makes the catalyst free from being heated together with the reaction product when the reaction product is separated, so that the catalyst can be avoided from deteriorating by heat, or from being poisoned by heat because of the reaction product or its decomposition product, making it possible to elongate the lifetime of the catalyst.

The water-insoluble organic medium can be exemplified by aromatic hydrocarbons such as benzene, toluene, xylene and cumene, and aliphatic hydrocarbons such as hexane, octane, cyclohexane and methylcyclohexane. It may be used in an amount of from 1/10 to 10/1 times by volume, and preferably from 1/5 to 5/1 times by volume of the reaction mixture.

In order to accelerate the layer separation, it is also possible to add water.

In order to accelerate the release of carbon dioxide gas, the nonionization of the catalyst and the extraction with the water-insoluble organic medium may preferably be carried out at a temperature of from 70° to 110° C. These may also be carried out under reduced pressure.

2-c)
Next, the catalyst transferred to the water-insoluble organic medium by extraction is ionized by the above process of reversible nonionization according to the second mode of the present invention, and the resulting ionized catalyst is transferred to an aqueous medium by extraction. At this time, the water-soluble ethylenically unsaturated compound is previously dissolved in the aqueous medium, whereby it becomes possible to again simply carry out the hydroformylation, so that the recycling of the catalyst can be achieved with ease.

The aqueous medium may be used in an amount of from 1/10 to 10/1 times by volume, and preferably from 1/5 to 5/1 times; by volume of the reaction mixture.

The hydroformylation product (an aldehyde) separated by extraction can be further purified by usual means such as crystallization or distillation.

In the present invention, the ethylenically unsaturated compound subjected to the hydroformylation can be exemplified by a vast range of ethylenically unsaturated compounds, including straight-chain, branched or cyclic, terminal or internal olefins having at least two carbon atoms, e.g., unsaturated aliphatic hydrocarbons such as ethylene, propylene, 1-butene, 1-pentene, 1-hexene, 1-heptene, 1-octene, 1-nonene, 2-butane, isobutene, 2-octene, 1,7-octadiene, vinyl cylohexene, dicyclopentadiene, cyclooctadiene, butadiene polymers and isoprene polymers, styrenes such as styrene, $\alpha$-methylstyrene, $\beta$-methylstyrene, alkyl group nuclear-substituted styrenes and divinybenzene, unsaturated alcohols such as allyl alcohol, methallyl alcohol, crotyl alcohol, 2-butene-1,4-diol, 3-methyl-3-buten-1-ol, 7-octen-1-ol and 2,7-octadienol, functional group-containing olefins such as vinyl acetate, allyl acetate, methyl acrylate, methyl methacrylate and 7-octen-1-al, and olefins with inorganic salt residual groups such as sodium allylsulfonate and sodium styrenesulfonate.

In the two modes of hydroformylation of the present invention, the catalyst is ionized or nonionized so that it can be selectively extracted, and the hydroformylation reaction mixture is separated into a product-containing layer and a catalyst-containing layer. This separation may be carried out in the presence of an inert gas such as nitrogen gas or a carbon monoxide/hydrogen mixed gas. When the layers are not well separated at the time of the extraction of the catalyst, it is preferable to use centrifugation in combination so that the layer separation can be accelerated.

Repetitions of the hydroformylation and the recovery of catalysts may result in a loss of catalysts at a level that can not be ignored, but the addition of catalyst components enables maintenance of the reaction rate with ease.

As described above, in the processes of hydroformylation according to the fourth and fifth modes of the present invention, the complex in which the ligand organic phosphorus compound having at least one tertiary amine residual group and at least one tertiary phosphorus residual group is coordinated to the centerel metal of the rhodium compound having a catalytic action that accelerates the hydroformylation is used as a hydroformylating catalyst.

Meanwhile, by the process of reversible ionization according; to the second mode of the present invention, the tertiary amine residual group of this organic phosphorus compound is converted into ammonium carbonate by allowing the compound to react with water and carbon dioxide gas to ionize tile catalyst. By the process of reversible nonionization according to the third mode of the present invention, the carbon dioxide gas is released from the ammonium carbonate residual group of the catalyst thus ionized, to convert it into tertiary amine to nonionize the catalyst. Thus, it becomes possible to reversibly ionize or nonionize the rhodium-containing catalyst according to the first mode of the present invention. Hence, the hydroformylating catalyst can be arbitrarily dissolved in or transferred by extraction, to the water-insoluble organic medium or dissolved in or transferred by extraction, to the aqueous medium.

Thus, in the processes of hydroformylation according to the fourth and fifth modes of the present invention, the utilization of the process of reversible ionization or nonionization of the rhodium-containing catalyst makes it possible to ionize or nonionize the catalyst in accordance with the properties of the ethylenically unsaturated compounds used, whichever the ethylenically unsaturated compounds are water-soluble or water-insoluble, and to bring the catalyst into the ethylenically unsaturated compounds; in a uniform solution.

After the reaction has been completed, the catalyst is brought into an ionic state reverse to that at the time of hydroformylation. Hence, it becomes possible at the same time to selectively extract, separate and recover the catalyst from the hydroformylation reaction mixture and to separate the reaction product.

The catalyst in the extract is further brought into a reverse ionic state, i.e., into the same ionic state as that at the time of hydroformylation. Hence, it becomes possible to allow the extract as it is to react with carbon monoxide and hydrogen to effect hydroformylation. Thus, it becomes possible to simply recycle the catalyst. It therefore becomes possible to produce corresponding aldehydes from ethylenically unsaturated compounds by hydroformylation at a low production cost in an industrially advantageous manner.

The rhodium-containing catalyst according to the sixth mode of the present invention will be described below.

The, rhodium-containing catalyst according to the sixth mode of the present invention further comprises, in addition to the component-(a) rhodium compound and the component-(b) organic phosphorus compound previously described in the first mode thereof, a component-(c) acidic compound with which at least part of the tertiary amine residual group of the organic phosphorus compound is converted into ammonium ions. In the rhodium-containing catalyst according to the sixth mode, this acidic compound converts at least part of the tertiary amine residual group into ammonium ions. Hence, the rhodium-containing catalyst comprised of the rhodium compound to which the ligand organic phosphorus compound(s) converted into ammonium ions is/are coordinated becomes water-soluble, so that it becomes possible to recover the catalyst components in an aqueous layer when the reaction mixture is brought into contact with water after the hydroformylation has been completed. In this case, the reaction product can also be separated at the same time when this recovery is operated, so long as the reaction product obtained by the hydroformylation is water-insoluble.

The recovery of the catalyst by means of extraction also makes the catalyst free from being heated together with the reaction product when the reaction product is separated, so that the catalyst can be avoided from deteriorating by heat, or from being poisoned by heat because of the reaction product or its decomposition product, making it possible to elongate the lifetime of the catalyst.

Any residue formed after removal of water by evaporation in the aqueous layer collected may be circulated to a hydroformylation reaction vessel so that it can be recycled and again used as a hydroformylating catalyst.

The rhodium-containing catalyst according to the sixth mode of the present invention, comprising the rhodium-containing catalyst comprised of the rhodium compound to which the ligand organic phosphorus compound(s) converted into ammonium ions is/are coordinated has a much better solubility in hydrocarbon type ethylenically unsaturated compounds such as octene, than the hydroformylating catalysts to the central metals of which the conventional water-soluble ligand organic phosphorus compounds containing monosulfonated salt residual groups are coordinated. Hence, the molar ratio of phosphorus to rhodium in the reaction system of hydroformylation can be made higher, and also the ethylenically unsaturated compounds subjected to hydroformylation can be greatly expanded in their scope of application. Moreover, it becomes unnecessary to use any polar solvents in principle or, if any, it is unnecessary to use them in a large quantity.

The component-(c) acidic compound is, as previously described a compound with which the tertiary amine residual group of the organic phosphorus compound having at least one tertiary amine residual group and at least one tertiary phosphorus residual group is converted into ammonium ions. It can be used under appropriate selection from those which are not inhibitory to the progress of hydroformylation, and may be either a Br$\phi$nsted acid or a Lewis acid. Such an acidic compound may include organic carboxylic acids as exemplified by monocarboxylic acids, dicarboxylic acids or polycarboxylic acids having 1 to 20 carbon atoms such as formic acid, acetic acid, propionic acid, butanoic acid, succinic acid, adipic acid and azelaic acid, phosphoric acids such as $H_3PO_4$, $NaH_2PO_4$, $KH_2PO_4$, $Na_2HPO_4$ and $K_2HPO_4$, boric acids such as $H_3BO_3$ and $NaH_2BO_3$, sulfonic acids such as benzenesulfonic acid and toluenesulfonic acid, and carbonic acids, any of which can be used.

In the hydroformylating catalyst according the sixth mode of the present invention, the component-(b) organic phosphorus compound may preferably be used in a gram atomic weight of from 1 to 10,000 g, and more preferably from 10 to 1,000 g, in terms of phosphorus atoms, based on 1 gram atom of the component-(a) rhodium compound in terms of rhodium atoms. Use of the organic phosphorus compound in an amount smaller than this lower limit may damage the stability of the catalyst. On the other hand, its use in an amount larger than this upper limit may result in a decrease in the reaction rate.

The component-(c) acidic compound may be used in an amount of at least 0.1 equivalent weight, and preferably from 0.3 to 5 equivalent weights, based on 1 equivalent weight of the tertiary amine residual group of the component-(b) organic phosphorus compound. Use of the acidic compound in an amount less than 0.1 equivalent weight may cause a serious decrease in recovery rate when catalyst components are recovered in contact with water.

The rhodium-containing catalyst according to the sixth mode of the present invention may be prepared by separately charging the components (a), (b) and (c) into the hydroformylation reaction system so that the three components react in that system to form a complex. Alternatively, it may also be prepared by dissolving the respective components in water to allow them to react therein to form a complex, and then removing the water from the resulting mixture, followed by drying.

The rhodium-containing catalyst according to the sixth mode of the present invention can be particularly preferably used when corresponding aldehydes are produced by hydroformylation of ethylenically unsaturated compounds including straight-chain, branched or cyclic, terminal or internal olefins having at least two carbon atoms, e.g., unsaturated aliphatic hydrocarbons such as ethylene, propylene, 1-butene, 1-pantene, 1-hexene, 1-heptene, 1-octene, 1-nonene, 2-butene, isobutene, 2-octene, 1,7-octadiene, vinyl cylohexene, cyclooctadiene, dicyclopentadiene, butadiene polymers and isoprene polymers, styrenes such as styrene, $\alpha$-methylstyrene, $\beta$-methylstyrene, alkyl group nuclear-substituted styrenes and divinybenzene, unsaturated alcohols such as allyl alcohol, crotyl alcohol, 3-methyl-3-buten-1-ol, 7-octen-1-ol and 2,7-octadienol, and functional group-containing olefins such as vinyl acetate, allyl acetate, methyl acrylate, methyl methacrylate and 7-octen-1-al. The process fop producing aldehydes in this way also constitutes part of the present invention.

The process for producing an aldehyde according to the seventh mode of the present invention will be described below.

The process for producing an aldehyde according to the seventh mode of the present invention comprises the step of allowing an ethylenically unsaturated compound to react with carbon monoxide and hydrogen to carry out hydroformylation to thereby convert it into a corresponding aldehyde, where the rhodium-containing catalyst according to the sixth mode of the present invention as described above is used. Other constitution of the present invention may be the same as the conventional process.

The hydroformylation in the process for producing an aldehyde according to the seventh mode of the present invention can be carried out in the following way. The ethylenically unsaturated compound and the rhodium-containing catalyst of the present invention are charged into a reactor such as a stirred tank reactor or a bubble column reactor, and a mixed reaction gas of hydrogen and carbon monoxide ($H_2/CO$, preferably in a molar ratio of about 0.5 to 5) is fed into this reactor at a pressure of usually from 1 to 300 atm, and preferably from 5 to 100 atm, followed by heating at usually from 20° to 160° C., and preferably from 50° to 140° C., with stirring, where the reaction may be carried out by a continuous method or a batch method.

In this hydroformylation, the rhodium-containing catalyst may preferably be in a concentration of a milligram atomic weight ranging from 0.001 to 10 mg, and more preferably from 0.005 to 5 mg, in terms of rhodium atoms, per liter of the reaction solution. Use of the rhodium-containing catalyst in an amount smaller than this lower limit may make the reaction rate excessively low, and on the other hand even its use in an amount larger than the upper limit can not make the reaction rate effectively high, rather resulting in an excessive increase in the cost of the catalyst.

In the case of a unidentate compound, the organic phosphorus compound in the reaction solution may preferably be in a concentration, which may vary depending on the type of the rhodium compound, of a milligram atomic weight ranging from 0.1 to 200 mg, and more preferably a milligram atomic weight ranging from 1 to 100 mg, in terms of rhodium atoms, per liter of the reaction solution. In the case of a bidentate or higher organic phosphorus compound, the compound may preferably be used in an amount ranging from 0.1- to 5-fold mols based on the rhodium atoms. Its use in a concentration outside this proper range can not make the present invention effective.

In this hydroformylation, a solvent inert to the ethylenically unsaturated compound and the reaction product may preferably be used when the ethylenically unsaturated compound, the reaction product and the phosphorus compound or acidic compound can not form a uniform solution. It can be exemplified by aromatic compounds such as benzene, toluene and xylene, aliphatic hydrocarbons such as hexane, octane and cyclohexane, ethers such as diethyl ether and diphenyl ether, ketones such as cyclohexanone and methyl isobutyl ketone, esters such as dioctyl phthalate and ethyl acetate, and non-protonic polar solvents such as dimethyl sulfoxide, N-methylpyrrolidone, sulfolane and dimethyl formamide. Any of these solvents may be used alone or in combination of two or more kinds.

After the hydroformylation has been completed, the intended aldehyde can be isolated from the reaction mixture by conventionally known methods. For example, a reaction mixture formed after the hydroformylation has been completed may be heated and distilled under reduced pressure, or may be cooled to carry out crystallization, whereby the intended aldehyde can be obtained. From evaporation residues, the rhodium-containing catalyst according to the sixth mode of the present invention can be recovered.

Alternatively, taking note of the fact that the rhodium-containing catalyst according to the sixth mode of the present invention is water-soluble as previously stated, the hydroformylation reaction mixture may be brought into contact with water, whereby the rhodium-containing catalyst is transferred to the aqueous layer by extraction so that the catalyst is removed from the reaction mixture, and then the intended aldehyde can be obtained from the organic layer. In this case, it is unnecessary to excessively heat the reaction product, and hence the reaction product can be prevented from undergoing decomposition or changes of properties.

The rhodium-containing catalyst transferred to the aqueous layer by extraction can be recovered from that aqueous layer by removing water in a conventional manner, e.g., by concentration under reduced pressure. The rhodium-containing catalyst thus recovered can be recycled as a catalyst used when aldehydes are again produced. Thus, the process for recovering the rhodium-containing catalyst constitutes part of the present invention.

The process for recovering the rhodium-containing catalyst according to the eighth mode of the present invention will be described below in detail.

In the process for recovering the rhodium-containing catalyst according to the eighth mode of the present invention, water is first added to the hydroformylation reaction mixture. In this addition, there are no particular limitations on the proportion of the water to the reaction mixture. Taking account of the operability and the solubility of water in the catalyst, their proportion may preferably be 1/20 to 2/1 in volume ratio.

Next, the reaction mixture is brought into contact with the water by stirring or the like to extract the rhodium-containing catalyst with water. This extraction may preferably be carried out at a temperature of from 20° to 90° C., and also may preferably be carried out in an atmosphere of inert gas such as nitrogen, helium or argon or a hydrogen/carbon monoxide mixed gas.

Incidentally, there is a possibility that the catalyst deteriorates in instances in which almost all the water has been removed from the aqueous layer containing the rhodium-containing catalyst, by concentration under reduced pressure or the like so that the reaction solution does not become non-uniform when the rhodium-containing catalyst recovered is circulated into the reaction vessel. Accordingly, in order to avoid an excessive concentration that is problematic in view of the stability of catalysts, a polar solvent having a higher boiling point than water may preferably be transferred together with the catalyst component to the aqueous layer by extraction. Hence, such a polar solvent may preferably be used in advance as the solvent used when the hydroformylation is carried out. Such a polar solvent can be preferably exemplified by non-protonic polar solvents such as dimethyl sulfoxide, N-methylpyrrolidone, sulfolane, dimethyl formamide and polyethylene glycol dimethyl ether.

When the polar solvent is used for such purpose, its use in excess may cause a decrease in the volumetric efficiency of the reaction, and is not preferable in view of productivity. Accordingly, the polar solvent in the hydroformylation reaction mixture should preferably be in a concentration of 80 w/v % or less, and more preferably 40 w/v % or less.

Next, after the operation as described above, the reaction mixture is separated into an upper layer, the organic layer containing the hydroformylation reaction product, and a lower layer, the aqueous layer which is an extraction layer containing the catalyst component (and a polar solvent when the polar solvent is used). In this instance, if the organic layer and the aqueous layer are not well separated even after the extraction has been carried out with water on the hydroformylation reaction mixture followed by standing, centrifugation may preferably be carried out in combination so that the layer separation can be promoted. It is also preferable to add a hydrocarbon with a smaller specific gravity than water, such as hexane or cylclohexane.

When the extraction is operated, any presence of solvents in a large quantity, such as alcohols that are miscible with water, may make it hard to remove water. Hence, it is preferred not to use such solvents. Accordingly, it is preferable to avoid using such solvents as the solvents used when the hydroformylation is carried out. The organic layer also contains, in addition to the reaction product, an unreacted ethylenically unsaturated compound and a small amount of rhodium-containing catalyst. Hence, in order to increase the recovery of the catalyst, it is preferable to wash the organic layer with water and to put the washing water and the aqueous layer together.

Next, the rhodium-containing catalyst can be recovered in a concentrate obtained after removal of water from the resulting aqueous layer. In this case, the water can be removed by a known method. For example, the water can be removed by evaporation. This evaporation may preferably be carried out at a temperature as low as possible so that the rhodium-containing catalyst can be prevented from undergoing thermal deterioration or the like. For example, evaporation under reduced pressure may preferably be carried out under conditions of a temperature of from 30° to 100° C. and a pressure of from 10 to 500 mmHg. In this case, the water should be evaporated to such an extent that no water separated is present in the reaction system when the condensate containing the catalyst is recycled in the hydroformylation reaction mixture.

If part of the polar solvent or part of the acidic compound is lost during the evaporation of the water, the polar solvent or the acidic compound may be supplemented to a recovery in a quantity corresponding to that of what has been lost, so that it become possible to recycle the catalyst. A concentrated solution obtained in this way may be kept in a temperature range of from about 30° to 70° C., whereby the catalyst can be preferably recycled while preventing its deterioration. Thus, this can be a catalyst recovery process advantageous also from industrial viewpoint.

Repetitions of the hydroformylation and the recovery of catalysts may result in a loss of catalysts at a level that can not be ignored, but the addition of catalyst components enables easy maintenance of the reaction rate.

As described above, the rhodium-containing catalyst according to the sixth mode of the present invention has been stabilized because of the ligand organic phosphorus compound having at least one tertiary amine residual group and at least one tertiary phosphorus residual group, coordinated to the metal ion of the rhodium compound having a catalytic action that accelerates the hydroformylation. Moreover, at least part of the tertiary amine residual group of the organic phosphorus compound has been converted into ammonium ions by means of the acidic compound. Hence, the catalyst having been converted into ammonium ions can dissolve in non-polar ethylenically unsaturated compounds to a certain extent, and gains the properties that it can also dissolve in water. Thus, the rhodium-containing catalyst according to the sixth mode of the present invention makes it possible to carry out hydroformylation of a vast range of non-polar or polar ethylenically unsaturated compounds without using polar solvents in a large quantity. Since the catalyst has also gained water-solubility, it becomes possible to extract the catalyst with water from the reaction mixture for its recovery.

In the process for producing an aldehyde according to the seventh mode of the present invention, the above catalyst according to the sixth mode of the present invention is used. Hence, corresponding aldehydes can be produced from a vast rage of ethylenically unsaturated compounds. When the reaction product aldehydes are water-insoluble water may be added to the reaction mixture after the reaction has been completed, so that it becomes possible to separate the reaction product from the catalyst with ease. It therefore becomes possible to prevent reaction products from undergoing decomposition or changes of properties when they are purified.

The aqueous solution of the rhodium-containing catalyst according to the sixth mode of the present invention which has been extracted with water can be readily recovered by the process for recovering a catalyst according to the eighth mode of the present invention, and hence it becomes possible to recycle the catalyst. Thus, it becomes possible to produce corresponding aldehydes from ethylenically unsaturated compounds by hydroformylation at a low production cost in an industrially advantageous manner.

EXAMPLES

The the present invention will be described below in greater detail by giving Examples. The present invention is by no means limited to these Examples.

Example 1

Into a 300 ml capacity magnetic stirring autoclave having a gas inlet and a sampling outlet, 2.58 mg (0.01 mmol) of dicarbonyl acetylacetonate rhodium, 433 mg (1 mmol) of tri(p-N,N-dimethylaminomethylphenyl)-phosphine, 20 g (0.139 mol) of sodium allyl sulfonate and 90 g of water were charged in the manner they did not come in touch with air, and carbon dioxide gas was fed into the autoclave until its inside reached a pressure of 10 kg/cm$^2$G. Thus a uniform solution was formed.

Subsequently, a hydrogen/carbon monoxide 1/1 mixed gas was continuously fed into the autoclave to provide a total pressure of 60 kg/cm$^2$G. While maintaining this pressure, the reaction mixture was stirred and its internal temperature was raised to 80° C. over a period of 20 minutes. In this state, hydroformylation was carried out for 5 hours. As a result, a hydroformylation product (a mixture of sodium 4-sulfobutanal and sodium 3-sulfo-2-methylpropanal) was obtained in a yield of 38%.

Next, the reaction mixture in the autoclave was pressure-fed into a 1 liter capacity three-necked flask having a reflux device, in the manner it did not come in touch with air, and 100 g of toluene was further added thereto in the manner it did not come in touch with air. While maintaining the temperature inside this three-necked flask at 90° C., nitrogen gas was flowed at a rate of 1 liter/hr, and stirring was carried out for 2 hours while releasing carbon dioxide gas. The stirring was stopped, and the resulting reaction mixture was separated into two layers, where the lower layer aqueous layer was drawn out.

To the remaining upper layer toluene layer containing the catalyst, 20 g (0.139 mol) of sodium allyl sulfonate and 90 g of water were added. The resulting aqueous mixture was charged into the autoclave in the manner it did not come in touch with air, and the inside of the autoclave was replaced with carbon dioxide gas, followed by stirring at 20° C. for 1 hour while the inside was maintained at a pressure of 10 kg/cm²G with carbon dioxide gas. The stirring was stopped, and the reaction mixture was pressure-fed into a 1 liter capacity separating funnel whose inside had been replaced with a hydrogen/carbon monoxide 1/1 mixed gas, followed by standing so as to be separated into two layers. The lower layer aqueous solution was passed into the autoclave in the manner it did not come in touch with air, where hydroformylation was carried out under the same conditions as the first reaction. As a result, a hydroformylation product was obtained in a yield of 43%.

Example 2

Into a 300 ml capacity magnetic stirring autoclave having a gas inlet and a sampling outlet, 2.58 mg (0.01 mmol) of dicarbonyl acetylacetonate rhodium, 1.08 g (2.5 mmol) of tri(p-N,N-dimethylaminomethylphenyl)-phosphine and 70 g of 1-octene were charged in the manner they did not come in touch with air, and the pressure inside the autoclave was set at a pressure of 20 kg/cm²G using a hydrogen/carbon monoxide 2/1 mixed gas. While maintaining this pressure, an off-gas was flowed at a rate of 15 liters/hr, and the internal temperature was raised to 90° C. over a period of 20 minutes with stirring. In this state, hydroformylation was carried out for 5 hours. The starting material 1-octene was in a conversion of 92%, and the hydroformylation was in a selectivity of 95%. The aldehyde produced had a straight-chain percentage of 80%.

Next, the hydrogen/carbon monoxide mixed gas in the autoclave was released until its internal pressure became equal to the atmospheric pressure. Thereafter, 200 ml of water was charged into the autoclave in the manner it did not come in touch with air, and its inside was replaced with carbon dioxide gas, followed by stirring at 25° C. for 3 hours while the inside was maintained at a pressure of 10 kg/cm²G with carbon dioxide gas. After the stirring was stopped, the reaction mixture was passed into a separating bath in the manner it did not come in touch with air, and separated into two layers.

The lower layer aqueous solution was passed into a 1 liter capacity three-necked flask having a reflux device, in the manner it did not come in touch with air, and 70 g of 1-octane was further added. The temperature inside this three-necked flask was maintained at 80° C., and nitrogen gas was flowed at a rate of 2 liters/hr, where stirring was carried out for 2 hours while releasing carbon dioxide gas. The stirring was stopped, and the resulting reaction mixture was separated into two layers. Then, the upper layer 1-octene, containing the catalyst component, was passed into the autoclave in the manner it did not come in touch with air, where hydroformylation was carried out under the same conditions as the first reaction. As a result, the starting material 1-octene was in a conversion of 86%, and the hydroformylation was in a selectivity of 95%. The aldehyde produced had a straight-chain percentage of 80%.

Example 3

Into a 300 ml capacity magnetic stirring autoclave having a gas inlet and a sampling outlet, 1,935 mg (0.0075 mmol) of dicarbonyl acetylacetonate rhodium, 162.4 mg (0,375 mmol) of tri(p-N,N-dimethylaminomethylphenyl) phosphine and 64 g of 7-octen-1-al (containing 10% by weight of n-octanal) were charged in the manner they did not come in touch with air, and the pressure inside the autoclave was set at a pressure of 90 kg/c²G using a hydrogen/carbon monoxide 1/1 mixed gas. While maintaining this pressure, the internal temperature was raised to 100° C. over a period of 20 minutes. In this state, hydroformylation was carried out for 30 minutes. As a result, the starting material 7-octen-1-al was in a conversion of 79%.

Next, the hydrogen/carbon monoxide mixed gas in the autoclave; was released until its internal pressure became equal to the atmospheric pressure. Thereafter, 100 ml of water was charged into the autoclave in the manner it did not come in touch with air, and its inside was replaced with carbon dioxide gas, followed by stirring at 20° C. for 3 hours while the inside was maintained at a pressure of 12 kg/cm²G with carbon dioxide gas. After the stirring was stopped, the reaction mixture was passed into a separating bath kept in an atmosphere of hydrogen/carbon monoxide gas, in the manner it did not come in touch with air, followed by centrifugation (10,000 G, 10 minutes) to separate it into two layers.

The lower layer aqueous solution was passed a 1 liter capacity three-necked flask having a reflux device, in the manner it did not come in touch with air, and 64 G of 7-octen-1-al (containing 10% by weight of n-octanal) was further added. The temperature inside this three-necked flask was maintained at 90° C., and nitrogen gas was flowed at a rate of 1 liter/hr, where stirring was carried out for 2 hours while releasing carbon dioxide gas. The stirring was stopped, and the resulting reaction mixture was separated into two layers. Then, the upper layer 7-octen-1-al, containing the catalyst component, was passed into the autoclave in the manner it did not come in touch with air, where hydroformylation was carried out under the same conditions as the first reaction. The starting material 7-octen-1-al was in a conversion of 66%.

Example 4

Into a 300 ml capacity magnetic stirring autoclave having a Gas inlet and a sampling outlet, 1.548 mg (0.006 mmol) of dicarbonyl acetylacetonate rhodium, 260 mg (0.6 mmol) of tri(p-N,N-dimethylaminomethylphenyl)phosphine and 102 G of 7-octen-1-al (containing 10% by weight of n-octanal) were charged in the manner they did not come in touch with air, and the pressure inside the autoclave was set at a pressure of 30 kg/cm²G using a hydrogen/carbon monoxide 1/1 mixed Gas. While maintaining this pressure, the internal temperature was raised to 90° C. over a period of 30 minutes with stirring. In this state, hydroformylation was carried out for 6 hours. The starting material 7-octen-1-al was in a conversion of 96%.

Next, the hydrogen/carbon monoxide mixed gas in the autoclave was released until its internal pressure became equal to the atmospheric pressure. Thereafter, 120 ml of water was charged into the autoclave in the manner it did not come in touch with air, and its inside was replaced with carbon dioxide gas, followed by stirring at 30° C. for 2 hours while the inside was maintained at a pressure of 6 kg/cm²G with carbon dioxide gas. After the stirring was stopped, the reaction mixture was passed into a separating bath kept in an atmosphere of hydrogen/carbon monoxide gas, in the manner it did not come in touch with air, followed by centrifugation (10,000 G, 10 minutes) to separate it into two layers.

The lower layer aqueous solution was a 1 liter capacity three-necked flask having a reflux device, in the manner it did not come in touch with air, and 102 g of 7-octen-1-al (containing 10% by weight of n-octanal)

was further added. The temperature inside this three-necked flask was maintained at 100° C., and nitrogen gas was flowed at a rate of 1 liter/hr, where stirring was carried out for 1 hour while releasing carbon dioxide gas. The stirring was stopped, and the resulting reaction mixture was separated into two layers. Then, the upper layer 7-octen-1-al, containing the catalyst component, was passed into the autoclave in the manner it did not come in touch with air, where hydroformylation was carried out under the same conditions as the first reaction. The starting material 7-octen-1-al was in a conversion of 81%.

Example 5

Into a 300 ml capacity magnetic stirring autoclave having a gas inlet and a sampling outlet, 1.29 mg (0,005 mmol) of dicarbonyl acetylacetonate rhodium, 43.3 mg (0.1 mmol) of tri(p-N,N-dimethylaminomethylphenyl) phosphine and 85 g of 7-octen-1-al (containing 10% by weight of n-octanal) were charged in the manner they did not come in touch with air, and the pressure inside the autoclave was set at a pressure of 30 kg/cm$^2$G using a hydrogen/carbon monoxide 1/1 mixed gas. The internal temperature was raised to 100° C. over a period of 30 minutes with stirring. In this state, hydroformylation was carried out for 3 hours. The starting material 7-octen-1-al was in a conversion of 89%.

Next, the hydrogen/carbon monoxide mixed gas in the autoclave was released until its internal pressure became equal to the atmospheric pressure. Thereafter, 50 ml of water was charged into the autoclave in the manner it did not come in touch with air, and its inside was replaced with carbon dioxide gas, followed by stirring at 40° C. for 5 hours while the inside was maintained at a pressure of 10 kg/cm$^2$G with carbon dioxide gas. After the stirring was stopped, the reaction mixture was passed into a separating bath kept in an atmosphere of hydrogen/carbon monoxide gas, in the manner it did not come in touch with air, followed by centrifugation (10,000 G, 10 minutes) to separate it into two layers.

The lower layer aqueous solution was a 1 liter capacity three-necked flask having a reflux device, in the manner it did not come in touch with air, and 85 g of 7-octen-1-al (containing 10% by weight of n-octanal) was further added. The temperature inside this three-necked flask was maintained at 80° C., and nitrogen gas was flowed at a rate of 1 liter/hr, where stirring was carried out for 1 hour while releasing carbon dioxide gas. The stirring was stopped, and the resulting reaction mixture was separated into two layers. Then, the upper layer starting material 7-octen-1-al, containing the catalyst component, was passed into the autoclave in the manner it did not come in touch with air, where hydroformylation was carried out under the same conditions as the first reaction. The starting material 7-octen-1-al was in a conversion of 61%.

Example 6

Into a 300 ml capacity magnetic stirring autoclave having a gas inlet and a sampling outlet, 1.29 mg (0.005 mmol) of dicarbonyl acetylacetonate rhodium, 1.08 g (2.5 mmol) of tri(p-N,N-dimethylaminomethylphenyl) phosphine and 85 g of 2,7-octadienol were charged in the manner they did not come in touch with air, and the pressure inside the autoclave was set at a pressure of 15 kg/cm$^2$G using a hydrogen/carbon monoxide 3/1 mixed gas. While maintaining this pressure, an off-gas was flowed at a rate of 15 liters/hr, and the internal temperature was raised to 85° C. over a period of 20 minutes with stirring. In this state, hydroformylation was carried out for 4.5 hours. The starting material 2,7-octadienol was in a conversion of 62%, and 9-hydroxy-7-nonen-1-al was in a yield of 43%.

Next, the hydrogen/carbon monoxide mixed gas in the autoclave was released until its internal pressure became equal to the atmospheric pressure. Thereafter, 100 ml of water was charged into the autoclave in the manner it did not come in touch with air, and its inside was replaced with carbon dioxide gas, followed by stirring at 20° C. for 3 hours while the inside was maintained at a pressure of 15 kg/cm$^2$G with carbon dioxide gas. After the stirring was stopped, the reaction mixture was passed into a separating bath kept in an atmosphere of hydrogen/carbon monoxide gas, in the manner it did not come in touch with air, followed by centrifugation (10,000 G, 30 minutes) to separate it into two layers.

The lower layer aqueous solution was a 1 liter capacity three-necked flask having a reflux device, in the manner it did not come in touch with air, and 85 g of 2,7-octadienol was further added. The temperature inside this three-necked flask was maintained at 80° C., and nitrogen gas was flowed at a rate of 1 liter/hr, where stirring was carried out for 2 hours while releasing carbon dioxide gas. The stirring was stopped, and the resulting reaction mixture was separated into two layers. Then, the upper layer starting material 2,7-octadienol, containing the catalyst component, was passed into the autoclave in the manner it did not come in touch with air, where hydroformylation was carried out under the same conditions as the first reaction. The starting material 2,7-octadienol was in a conversion of 58%, and 9-hydroxy-7-nonen-1-al was in a yield of 40%.

Example 7

Into a 300 ml capacity magnetic stirring autoclave having a gas inlet and a sampling outlet, 1.548 mg (0.006 mmol) of dicarbonyl acetylacetonate rhodium, 260 mg (0.6 mmol) of tri(p-N,N-dimethylaminomethylphenyl) phosphine and 102 g of 2,7-octadienol were charged in the manner they did not come in touch with air, and the pressure inside the autoclave was set at a pressure of 30 kg/cm$^2$G using a hydrogen/carbon monoxide 3/1 mixed gas. While maintaining this pressure, an off-gas was flowed at a rate of 15 liters/hr, and the internal temperature was raised to 100° C. over a period of 20 minutes with stirring. In this state, hydroformylation was carried out for 4 hours. The starting material 2,7-octadienol was in a conversion of 70%, and 9-hydroxy-7-nonen-1-al was in a yield of 44%.

Next, the hydrogen/carbon monoxide mixed gas in the autoclave was released until its internal pressure became equal to the atmospheric pressure. Thereafter, 60 ml of water was charged into the autoclave in the manner it did not come in touch with air, and its inside was replaced with carbon dioxide gas, followed by stirring for 1 hour while the inside was maintained at a pressure of 10 kg/cm$^2$G with carbon dioxide gas and while the internal temperature was maintained at 35° C. After the stirring was stopped, the reaction mixture was passed into a separating bath kept in an atmosphere of hydrogen/carbon monoxide gas, in the manner it did not come in touch with air, followed by centrifugation (10,000 G, 30 minutes) to separate it into two layers.

The lower layer aqueous solution was a 1 liter capacity three-necked flask having a reflux device, in the manner it did not come in touch with air, and 102 g of 2,7-octadienol was further added. The temperature inside this three-necked flask was maintained at 90° C., and helium gas was flowed at a rate of 1 liter/hr, where stirring was carried out for 1 hour while releasing carbon dioxide gas. The stirring was stopped, and the resulting reaction mixture was separated into two layers. Then, the upper layer 2,7-octadienol, containing the catalyst component, was passed into the autoclave in the manner it did not come in touch with air, where hydroformylation was carried out under the same conditions as the first reaction. The starting material 2,7-octadienol was in a conversion of 65%, and 9-hydroxy-7-nonen-1-al was in a yield of 41%.

Example 8

Into a 300 ml capacity magnetic stirring autoclave having a gas inlet and a sampling outlet, 1.29 mg (0.005 mmol) of dicarbonyl acetylacetonate rhodium, 43.3 g (0.1 mmol) of tri(p-N,N-dimethylaminomethylphenyl)-phosphine and 91 g of styrene were charged in the manner they did not come in touch with air, and the pressure inside the autoclave was set at a pressure of 90 kg/cm$^2$G using a hydrogen/carbon monoxide 1/1 mixed gas. While maintaining this pressure, the internal temperature was raised to 110° C. over a period of 20 minutes with stirring. In this state, hydroformylation was carried out for 6 hours. The starting material styfane was in a conversion of 72%, and the hydroformylation was in a selectivity of 98%. The aldehyde produced had a straight-chain percentage of 20%.

Next, the hydrogen/carbon monoxide mixed gas in the autoclave was released until its internal pressure became equal to the atmospheric pressure. Then, 25 ml of water and 50 ml of n-hexane were charged into the autoclave in the manner they did not come in touch with air, and its inside was replaced with carbon dioxide gas, followed by stirring at 25° C. for 1 hour while the inside was maintained at a pressure of 6 kg/cm$^2$G with carbon dioxide gas. After the stirring was stopped, the reaction mixture was transferred into a separating bath kept in an environment of carbon dioxide gas, in the manner it did not come in touch with air, and separated into two layers.

The lower layer aqueous solution was transferred into the autoclave in the manner it did not come in touch with air,, and 91 g of styrene was further added. The temperature inside this three-necked flask was maintained at 90° C., and nitrogen gas was flowed at a rate of 1 liters/hr, where stirring was carried out for 1 hour while releasing carbon dioxide gas. The stirring was stopped, and the resulting reaction mixture was separated into two layers. Then, the upper layer starting material styrene, containing the catalyst component, was passed into the autoclave in the manner it did not come in touch with air, where hydroformylation was carried out under the same conditions as the first reaction. The starting material styrene 1975 was in a conversion of 55%, and the hydroformylation was in a selectivity of 98%. The aldehyde produced had a straight-chain percentage of 20%.

Example 9

Into a 300 ml capacity magnetic stirring autoclave having a gas inlet and a sampling outlet, 2.58 mg (0.01 mmol) of dicarbonyl acetylacetonate rhodium, 217 mg (0.5 mmol) of tri(p-N,N-dimethylaminomethylphenyl)-phosphine, 44 g (0.5 mol) of 2-butene-1,4-diol and 59 g of water were charged in the manner they did not come in touch with air, and carbon dioxide gas was fed into the autoclave until its inside reached a pressure of 10 kg/cm$^2$G. Thus a uniform solution was formed.

Subsequently, a hydrogen/carbon monoxide 1/1 mixed gas was continuously fed into the autoclave to provide a total pressure of 80 kg/cm$^2$G. While maintaining this pressure, its internal temperature was raised to 60° C. over a period of 30 minutes. In this state, hydroformylation was carried out for 10 hours. As a result, 2-formyl-1,4-butanediol was obtained as a hydroformylation product in a yield of 30%.

Next, the reaction mixture in the autoclave was immediately cooled and pressure-fed into a 1 liter capacity three-necked flask having a reflux device, in the manner it did not come in touch with air, and 200 ml of toluene and 100 ml of water were further charged thereinto in the manner they did not come in touch with air. While nitrogen gas was flowed at a rate of 1 liter/hr, the temperature inside this three-necked flask was raised at a rate of 30° C. per hour until it reached 90° C., and, after it reached 90° C., the reaction mixture was further stirred for 1 hour while releasing carbon dioxide gas. The stirring was stopped, and the resulting reaction mixture was separated into two layers, where the lower layer aqueous layer was drawn out.

To the remaining upper layer toluene layer, containing the catalyst, 44 g (0.5 mol) of 2-butene-1,4-diol and 59 g of water were added. The resulting aqueous mixture was charged into the autoclave in the manner it did not come in touch with air, and the inside of the autoclave was replaced with carbon dioxide gas, followed by stirring at 25° C. for 2 hours while the inside was maintained at a pressure of 12 kg/cm$^2$G with carbon dioxide gas. The stirring was stopped, and the reaction mixture was pressure-fed into a 1 liter capacity separating funnel whose inside had been replaced with a hydrogen/carbon monoxide 1/1 mixed gas, followed by standing so as to be separated into two layers. The lower layer aqueous solution was passed into the autoclave in the manner it did not come in touch with air, where hydroformylation was carried out under the same conditions as the first reaction. As a result, 2-formyl-1,4-butanediol was obtained in a yield of 24%.

Example 10

Into a 300 ml capacity magnetic stirring autoclave having a gas inlet and a sampling outlet, 1.29 mg (0.005 mmol) of dicarbonyl acetylacetonate rhodium, 217 mg (0.5 mmol) of tri(p-N,N-dimethylaminomethylphenyl)-phosphine, 44 g (0.5 mol) of 2-butene-1,4-diol and 59 g of water were charged in the manner they did not come in touch with air, and carbon dioxide gas was fed into the autoclave until its inside reached a pressure of 10 kg/cm$^2$G. Thus a uniform solution was formed.

Subsequently, a hydrogen/carbon monoxide 1/1 mixed gas was continuously fed into the autoclave to provide a total pressure of 120 kg/cm$^2$G. While maintaining this pressure an also with stirring, its internal temperature was raised to 60° C. over a period of 30 minutes. In this state, hydroformylation was carried out for 6 hours. As a result, 2-formyl-1,4-butanediol was obtained as a hydroformylation product in a yield of 10%.

Next, the reaction mixture in the autoclave was immediately cooled and pressure-fed into a 1 liter capacity three-necked flask having a reflux device, in the manner it did not come in touch with air, and 168 g of 1-octene was further charged thereinto in the manner they did not come in touch with air. While nitrogen gas was flowed at a rate of 1 liter/hr, the temperature inside this three-necked flask was raised at a rate of 30° C. per hour until it reached 90° C., and, after it reached 90° C., the reaction mixture was further stirred for 1 hour while releasing carbon dioxide gas. The stirring was stopped, and the resulting reaction mixture was separated into two layers, where the lower layer aqueous layer was drawn out.

The remaining upper layer 1-octene, containing the catalyst, was charged into a 500 ml capacity magnetic stirring autoclave having a gas inlet and a sampling outlet, in the manner it did not come in touch with air, and its atmosphere was replaced with a hydrogen/carbon monoxide 1/1 mixed gas, and further maintained at a pressure of 120 kg/cm$^2$G, where the internal temperature was raised to 110° C. over a period of 20 minutes with stirring. In this state, hydroformylation was carried out for 4 hours. The starting material 1-octane was in a conversion of 91%, and the hydroformylation was in a selectivity of 98%. The aldehyde produced had a straight-chain percentage of 60%.

In the foregoing Examples 1 to 10, without regard to whether ethylenically unsaturated compounds are water-soluble or water-insoluble, the ethylenically unsaturated compounds can be subjected to hydroformylation to produce aldehydes at an industrially satisfactory reaction rate, without using nonaqueous polar solvents in large quantities. Moreover, the catalysts can be recovered at a high yield, and the catalyst thus recovered can be recycled.

Example 11

Into a 300 ml capacity magnetic stirring autoclave having a gas inlet and a sampling outlet, 25.8 mg (0.1 mmol) of dicarbonyl acetylacetonate rhodium as a catalyst, 866 mg (2 mmol) of tri(p-N,N-dimethylaminomethylphenyl) phosphine and 0.36 g (6 mmol) of acetic acid, as well as 70 g (0.6.25 mol) of 1-octene as an ethylenically unsaturated compound were charged in the manner they did not come in touch with air, and the inside of the autoclave was kept at a pressure of 25 kg/cm$^2$G using a hydrogen/carbon monoxide 3/1 mixed gas. Then, an off-gas was flowed at a rate of 15 liter/hr, and the internal temperature was raised to 80° C. with stirring. In this state, hydroformylation was carried out for 5 hours. The starting material 1-octene was in a conversion of 96%, and the end product 1-nonanal was in a yield of 60.9 g.

Subsequently, the reaction mixture was pressure-fed into a 200 ml three-necked flask having been thoroughly replaced with a hydrogen/carbon monoxide mixed gas (molar ratio: 3/1), in the manner it did not come in touch with air, and 20 ml of water was added thereto, followed by stirring for 20 minutes in an atmosphere of the mixed gas with the above composition while maintaining the internal temperature at 30° C. After the stirring was stopped, the lower layer aqueous layer was drawn out. To the remaining upper layer organic layer, 20 ml of water was again added, followed by stirring for 20 minutes in an atmosphere of the mixed gas with the above composition while maintaining the internal temperature at 30° C. After the stirring was stopped, the lower layer aqueous solution was drawn out, and was put together with the first aqueous layer. The resulting solution was passed into a 200 ml eggplant type flask kept in an atmosphere of nitrogen, which was set on a rotary evaporator. While this flask was immersed in a water bath kept at 70° C., the internal pressure of the flask was gradually dropped to 20 mmHg, where water was evaporated for 30 minutes. Thereafter, the resulting condensate was cooled together with the flask, and its inside was returned to a normal pressure using nitrogen gas. Thus, the catalyst was recovered.

In the flask containing the catalyst thus recovered, 70 g of 1-octene was added and mixed with stirring, and the mixture was again passed into the autoclave in the manner it did not come in touch with air, where hydroformylation was carried out under the same conditions as the first reaction. As a result, the starting material was in a conversion of 92%.

Example 12

Into a 300 ml capacity magnetic stirring autoclave having a gas inlet and a sampling outlet, 2.58 mg (0.01 mmol) of dicarbonyl acetylacetonate rhodium as a catalyst, 866 mg (2 mmol) of tri(p-N,N-dimethylaminomethylphenyl) phosphine, 0.72 g (12 mmol) of acetic acid, 77 g (0.55 mol) of 7-octen-1-al (purity: 90%; containing 10% of n-octanol) and 10 g of dimethyl sulfoxide were charged in the manner they did not come in touch with air, and the inside of the autoclave was kept at a pressure of 90 kg/cm$^2$G using a hydrogen/carbon monoxide 1/1 mixed gas. Then the internal temperature was raised to 80° C. with stirring. In this state, hydroformylation was carried out for 4 hours. The starting material 7-octen-1-al was in a conversion of 88%, and the end product 1,9-nonadinal was in a yield of 47.7 g.

Subsequently, the reaction mixture was pressure-fed into a 1 liter three-necked flask having been thoroughly replaced with a hydrogen/carbon monoxide mixed gas (molar ratio: 1/1), in the manner it did not come in touch with air, and 20 ml of water was added thereto, followed by stirring for 20 minutes in an atmosphere of the mixed gas with the above composition while maintaining the internal temperature at 30° C. After the stirring was stopped, the reaction mixture was passed into a separating bath kept in an atmosphere of hydrogen/carbon monoxide gas, followed by centrifugation (10,000 G, 10 minutes) to separate it into two layers. The lower layer aqueous layer was passed into a 200 ml eggplant type flask kept in an atmosphere of nitrogen, which was set on a rotary evaporator. While this flask was immersed in a water bath kept at 60° C., the internal pressure of the flask was gradually dropped to 15 mmHg, where water was evaporated for 15 minutes. Thereafter, the resulting condensate was cooled together with the flask, and its inside was returned to a normal pressure using nitrogen gas. Thus, the catalyst was recovered.

In the flask containing the catalyst thus recovered, 77 g of 7-octen-1-al was added and mixed with stirring, and the mixture was further passed into the autoclave in the manner it did not come in touch with air, where the reaction was carried out under the same conditions as the first one. The starting material was in a conversion of 80%.

Example 13

Into a 300 ml capacity magnetic stirring autoclave having a gas inlet and a sampling outlet, 6.44 mg (0.025 mmol) of dicarbonyl acetylacetonate rhodium, 433 mg (1 mmol) of tri(p-N,N-dimethylaminomethylphenyl)-phosphine, 120 mg (2 mmol) of acetic acid and 91 g (0.875 mol) of styrene were charged in the manner they did not come in touch with air, and the inside of the autoclave was kept at a pressure of 90 kg/cm$^2$G using a hydrogen/carbon monoxide 1/1 mixed gas. Then the internal temperature was raised to 100° C. with stirring. In this state, hydroformylation was carried out for 5 hours. The starting material styrene was in a conversion of 100%, and the end product 2-phenylpropanal was in a yield of 93.0 g.

Subsequently, the reaction mixture was pressure-fed into a 200 ml three-necked flask having been thoroughly replaced with a hydrogen/carbon monoxide mixed gas (molar ratio: 1/1), in the manner it did not come in touch with air, and 20 ml of water and 50 ml of hexane were added thereto, followed by stirring for 10 minutes in an atmosphere of the mixed gas with the above composition while maintaining the internal temperature at 30° C. After the stirring was stopped, the lower layer aqueous layer was drawn out, and it was passed into a 200 ml eggplant type flask kept in an atmosphere of nitrogen, which was set on a rotary evaporator. While this flask was immersed in a water bath kept at 70° C., the internal pressure of the flask was gradually dropped to 15 mmHg, where water was evaporated for 30 minutes. Thereafter, the resulting condensate was cooled together with the flask, and its inside was returned to a normal pressure using nitrogen gas. Thus, the catalyst was recovered.

In the flask containing the catalyst thus recovered, 91 g of styfane was added and mixed with stirring, and the mixture was again passed into the autoclave in the manner it did not come in touch with air, where hydroformylation was carried out under the same conditions as the first reaction. The starting material was in a conversion of 100%.

Example 14

Into a 300 ml capacity magnetic stirring autoclave having a gas inlet and a sampling outlet, 2.58 mg (0.01 mmol) of dicarbonyl acetylacetonate rhodium, 433 mg (1 mmol) of tri(p-N,N-dimethylaminomethylphenyl)-phosphine, 380 mg (2 mmol) of p-toluenesulfonic acid monohydrate, 76 g (0.60 mol) of 2,7-octadienol and 11 g of sulfolane were charged in the manner they did not come in touch with air, and the inside of the autoclave was kept at a pressure of 30 kg/cm$^2$G using a hydrogen/carbon monoxide 1/1 mixed gas. Then the internal temperature was raised to 90° C. with stirring. In this state, hydroformylation was carried out for 4 hours. The starting material 2,7-octadienol was in a conversion of 72%, and the end product 9-hydroxy-7-nonenol was in a yield of 30 g.

Subsequently, the reaction mixture was pressure-fed into a 0.5 liter three-necked flask having been thoroughly replaced with a hydrogen/carbon monoxide mixed gas (molar ratio: 1/1), in the manner it did not come in touch with air, and 20 ml of water and 50 ml of hexane were added thereto, followed by stirring for 20 minutes in an atmosphere of the mixed gas with the above composition while maintaining the internal temperature at 20° C. After the stirring was stopped, the reaction mixture was passed into a separating bath kept in an atmosphere of hydrogen/carbon monoxide gas, followed by centrifugation (10,000 G, 5 minutes) to separate it into two layers. The lower layer aqueous layer was passed into a 200 ml eggplant type flask kept in an atmosphere of nitrogen, which was set on a rotary evaporator. While this flask was immersed in a water bath kept at 60° C., the internal pressure of the flask was gradually dropped to 20 mmHg, where water was evaporated for 20 minutes. Thereafter, the resulting condensate was cooled together with the flask, and its inside was returned to a normal pressure using nitrogen gas. Thus, the catalyst was recovered.

In the flask containing the catalyst thus recovered, 76 g of 2,7-octadienol was added and mixed with stirring, and the mixture was further passed into the autoclave in the manner it did not come in touch with air, where the reaction was carried out under the same conditions as the first one. The starting material was in a conversion of 65%, and the end product 9-hydroxy-7-nonenol was in a yield of 27 g.

Example 15

Into a 300 ml capacity magnetic stirring autoclave having a gas inlet and a sampling outlet, 5.16 mg (0.021 mmol) of dicarbonyl acetylacetonate rhodium as a catalyst, 866 mg (2 mmol) of tri(p-N,N-dimethylaminomethylphenyl) phosphine, 360 mg (5 mmol) of acetic acid, 76 g (0.76 mol) of methyl methacrylate and 21 g of dimethyl sulfoxide were charged in the manner they did not come in touch with air, and the inside of the autoclave was kept at a pressure of 90 kg/cm$^2$G using a hydrogen/carbon monoxide 1/1 mixed gas. Then the internal temperature was raised to 80° C. with stirring. In this state, hydroformylation was carried out for 8 hours. The starting material methyl methacrylate was in a conversion of 81%, and the end product methyl 2-methyl-2-formylpropionate was in a yield of 68 g.

Subsequently, the reaction mixture was pressure-fed into a 0.5 liter three-necked flask having been thoroughly replaced with a hydrogen/carbon monoxide mixed gas (molar ratio: 1/1), in the manner it did not come in touch with air, and 25 ml of water and 100 ml of hexane were added thereto, followed by stirring for 15 minutes in an atmosphere of the mixed gas with the above composition while maintaining the internal temperature at 20° C. After the stirring was stopped, the reaction mixture was passed into a separating bath kept in an atmosphere of hydrogen/carbon monoxide gas with the above composition, followed by centrifugation (10,000 G, 10 minutes) to separate it into two layers. The lower layer aqueous layer was passed into a 200 ml eggplant type flask kept in an atmosphere of nitrogen, which was set on a rotary evaporator. While this flask was immersed in a water bath kept at 70° C., the internal pressure of the flask was gradually dropped to 20 mmHg, where water was evaporated for 30 minutes. Thereafter, the resulting condensate was cooled together with the flask, and its inside was returned to a normal pressure using nitrogen gas. Thus, the catalyst was recovered.

In the flask containing the catalyst thus recovered, 76 g of methyl methacrylate was added and mixed with stirring, and the mixture was further passed into the autoclave in the manner it did not come in touch with air, where the reaction was carried out under the same conditions as the first one. The starting material was in a conversion of 73%, and the end product methyl 2-methyl-2-formylpropionate was in a yield of 61 g.

In the foregoing Examples 11 to 15, the ethylenically unsaturated compounds can be subjected to hydroformylation to produce aldehydes at an industrially satisfactory reaction rate, without using nonaqueous polar solvents in large quantities. Moreover, the catalysts can be recovered at a high yield, and the catalyst thus recovered can be recycled.

What is claimed is:

1. A rhodium-containing catalyst comprising:
   (a) a rhodium compound which exhibits the catalytic action of accelerating the hydroformylation of an ethylenically unsaturated compound or which is capable of achieving such catalytic action under conditions of hydroformylation; and
   (b) an organic phosphorus compound having at least one tertiary amine residual group and at least one tertiary phosphorus residual group, having the ability of coordination to said rhodium compound.

2. The rhodium-containing catalyst according to claim 1, wherein said component-(b) organic phosphorus compound comprises a compound represented by any one of Formulas (1) to (4):

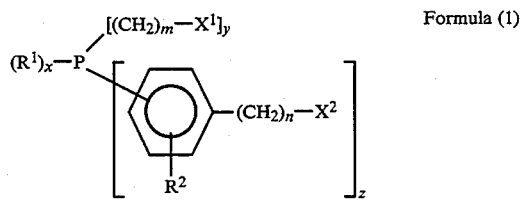

Formula (1)

wherein $R^1$ represents a hydrocarbon groups having 1 to 10 carbon atoms; represents a hydrogen atom, an alkyl group having 1 to 5 carbon atoms, a nitro group or a halogen atom; m is 1, 2 or 3, and n is 0 or 1; x is 0, 1 or 2, and y and z are each independently 0, 1, 2 or 3, provided that the sum of x, y and z is 3; and $X^1$ and $X^2$ each independently represent a hydrogen atom or —$NR^3R^4$, where $R^3$ and $R^4$ each independently represent an alkyl group having 1 to 4 carbon atoms, provided that $X^1$ and $X^2$ are not hydrogen atoms at the same time when both y and z are not 0, $X^2$ is —$NR^3R^4$ when y is 0, and $X^1$ is —$NR^3R^4$ when z is 0;

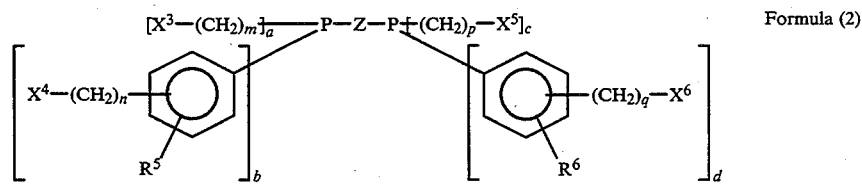

Formula (2)

wherein $R^5$ and $R^6$ each independently represent a hydrogen atom, an alkyl group having 1 to 5 carbon atoms, a nitro group or a halogen atom; m and n are as defined in Formula (1), p is 1, 2 or 3, and q is 0 or 1; a, b, c and d are each independently 0, 1 or 2, provided that the sum of a, b, c and d is 4; Z represents a divalent hydrocarbon group having 1 to 10 carbon atoms; and $X^3$, $X^4$, $X^5$ and $X^6$ each independently represent a hydrogen atom or —$NR^3R^4$ where $R^3$ and $R^4$ are as defined in Formula (1), provided that $X^3$, $X^4$ $X^5$ and $X^6$ are not hydrogen atoms at the same time when a, b, c and d are each 1, at least one of $X^4$, $X^5$ and $X^6$ is —$NR^3R^4$ when a is 0, at least one of $X^3$, $X^5$ and $X^6$ is —$NR^3R^4$ when b is 0, at least one of $X^3$, $X^4$ and $X^6$ is —$NR^3R^4$ when c is 0, and at least one of $X^3$, $X^4$ and $X^5$ is —$NR^3R^4$ when d is 0;

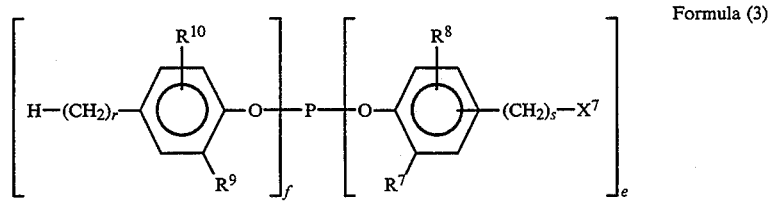

Formula (3)

wherein $R^7$ and $R^9$ each independently represent a hydrogen atom, an alkyl group having 1 to 6 carbon atoms or a phenyl group; $R^8$ and $R^{10}$ each independently represent a hydrogen atom, an alkyl group having 1 to 6 carbon atoms, a nitro group, or a halogen atom; r and s are each independently 0, 1, 2 or 3; e is 1, 2 or 3, and f is 0, 1 or 2, provided that the sum of e and f is 3; and $X^7$ represents —$NR^3R^4$ where $R^3$ and $R^4$ are as defined in Formula (1);

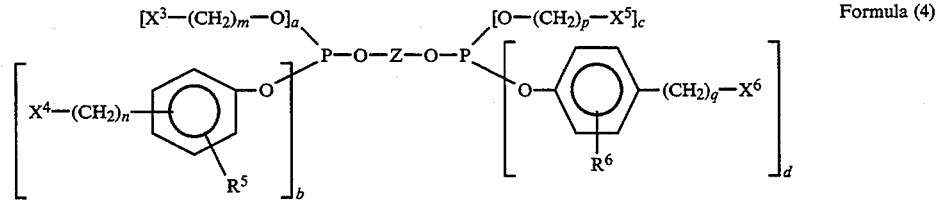

Formula (4)

wherein $R^5$, $R^6$, m, n, p, q, a, b, c, d, $X^3$, $X^4$, $X^5$, $X^6$ and Z are as defined in Formula (2).

3. The rhodium-containing catalyst according to claim 2, wherein said component-(b) organic phosphorus compound is selected from the group consisting of compounds; represented by the following formulas (5) to (22).

| | |
|---|---|
| $P[CH_2N(C_2H_5)_2]_3$ | (5) |
| $(C_4H_9)_2PCH_2N(CH_3)_2$ | (6) |
| $(C_4H_9)_2PCH_2CH_2N(CH_3)_2$ | (7) |

| | |
|---|---|
| $P[CH_2CH_2CH_2N(CH_3)_2]_3$ | (8) |
| $P[CH_2CH_2CH_2N(C_2H_5)_2]_3$ | (9) |
| $P[CH_2CH_2N(t-C_4H_9)_2]_3$ | (10) |
| $(C_8H_{17})P[CH_2N(CH_3)_2]_2$ | (11) |
| $(C_6H_{13})_2PCH_2CH_2CH_2N(CH_3)_2$ | (12) |
| $(C_6H_5)_2PCH_2N(CH_3)_2$ | (13) |
| $(C_6H_5)_2PCH_2CH_2N(CH_3)_2$ | (14) |
| $P[CH_2CH_2C_6H_4N(CH_3)_2]_3$ | (15) |
| $P[C_6H_4N(CH_3)_2]_3$ | (16) |
| $P[C_6H_4CH_2N(CH_3)_2]_3$ | (17) |
| $C_6H_5P[C_6H_4N(CH_3)_2]_2$ | (18) |
| $C_6H_5P[C_6H_4CH_2N(CH_3)_2]_2$ | (19) |
| $C_6H_5P[CH_2CH_2CH_2N(CH_3)_2]_2$ | (20) |
| $(C_6H_5)_2P[C_6H_4N(CH_3)_2]$ | (21) |
| $(C_6H_5)_2P[C_6H_4CH_2N(i-C_3H_7)_2]$ | (22) |

4. The rhodium-containing catalyst according to claim 1, wherein said component-(b) organic phosphorus compound is present in a gram atomic weight of from 1 g to 10,000 g in terms of phosphorus atoms, based on 1 gram atom of said component-(a) rhodium compound in terms of rhodium atoms.

5. The rhodium-containing catalyst according to claim 1, in the presence of which an ethylenically unsaturated compound is allowed to react with carbon monoxide and hydrogen to carry out hydroformylation.

6. A process of reversibly ionizing the rhodium-containing catalyst according to claim 1, said process comprising the step of bringing said catalyst into contact with water and carbon dioxide gas to cause them to react so that a tertiary amine residual group of said organic phosphorus compound is formed into an ammonium carbonate to ionize said catalyst.

7. A process of reversibly nonionizing the rhodium-containing catalyst having been reversibly ionized by the process according to claim 6, said process comprising the step of releasing carbon dioxide gas from said ionized catalyst to nonionize said ionized catalyst.

8. A process of hydroformylation comprising allowing a water-insoluble ethylenically unsaturated compound to react with carbon monoxide and hydrogen in the presence of a rhodium-containing catalyst to produce an aldehyde, wherein;

said process comprises the steps of ionizing a catalyst in a reaction mixture by the process according to claim 6 so that the catalyst can be separated from a water-insoluble hydroformylation product after the reaction, subsequently transferring the ionized catalyst to an aqueous layer by extraction, further nonionizing the catalyst contained in the aqueous layer by releasing carbon dioxide gas from said ionized catalyst to nonionize said ionized catalyst, and transferring the nonionized catalyst to a water-insoluble organic medium by extraction.

9. The process of hydroformylation according to claim 8, wherein said water-insoluble organic medium contains the water-insoluble ethylenically unsaturated compound, and carbon monoxide and hydrogen are fed into said medium to again carry out hydroformylation.

10. A process of hydroformylation comprising allowing a water-soluble ethylenically unsaturated compound to react with carbon monoxide and hydrogen in the presence of an ionized rhodium-containing catalyst to produce an aldehyde, wherein:

said rhodium-containing catalyst comprises the catalyst ionized by the process according to claim 6, and said process comprises the steps of nonionizing the catalyst ionized in a resulting reaction mixture, by releasing carbon dioxide gas from said ionized catalyst to nonionize said nonionized catalyst so that the catalyst is separated from a water-soluble hydroformylation product after the reaction, and transferring the nonionized catalyst to a water-insoluble organic medium by extraction.

11. The process of hydroformylation according to claim 10, wherein the water-insoluble organic medium containing the catalyst ionized by the process according to claim 10 is brought into contact with water containing a water-soluble ethylenically unsaturated compound, and the catalyst thus ionized is transferred to an aqueous layer by extraction, and carbon monoxide and hydrogen are fed into a resulting extract to again carry out hydroformylation.

12. The rhodium-containing catalyst according to any one of claim 1 to 4, which further comprises (c) an acidic compound with which at least part of the tertiary amine residual group of the organic phosphorus compound is converted into ammonium ions.

13. The rhodium-containing catalyst according to claim 12, wherein said component-(b) organic phosphorus compound is contained in a gram atomic weight of from 1 g to 10,000 g in terms of phosphorus atoms, based on 1 gram atom of said component-(a) rhodium compound in terms of rhodium atoms, and said component-(c) acidic compound is contained in an amount of at least 0.1 equivalent weight based on 1 equivalent weight of the tertiary amine residual group of said component-(b) organic phosphorus compound.

14. The rhodium-containing catalyst according to claim 12 or 13, in the presence of which an ethylenically unsaturated compound is allowed to react with carbon monoxide and hydrogen to carry out hydroformylation.

15. A process for producing an aldehyde, comprising the step of allowing an ethylenically unsaturated compound to react with carbon monoxide and hydrogen in the presence of a catalyst to carry out hydroformylation to obtain a reaction mixture containing a corresponding aldehyde, wherein said catalyst comprises the rhodium-containing catalyst according to claim 12.

16. The process for producing an aldehyde according to claim 15, wherein, when said ethylenically unsaturated compound is allowed to react with carbon monoxide and hydrogen in the presence of said catalyst, the reaction is carried out in the presence of a polar solvent having a higher boiling point than water.

17. The process for producing an aldehyde according to claim 16, wherein said polar solvent is selected from the group consisting of dimethyl sulfoxide, N-methylpyrrolidone, sulfolane, dimethylformamide and polyethylene glycol dimethyl ether.

18. The process for producing an aldehyde according to any one of claims 15 to 17, wherein said ethylenically unsaturated compound and said aldehyde obtained therefrom are substantially water-insoluble.

19. A process for recovering the rhodium-containing catalyst according to any one of claims 12 to 14, from the reaction mixture obtained by the process for producing an aldehyde according to claim 18, wherein the reaction mixture is brought into contact with water so that the rhodium-containing catalyst is transferred to an aqueous layer by extraction, and the water is removed from the resulting aqueous layer.

20. The rhodium-containing catalyst according to claim 1, wherein said rhodium compound is a rhodium oxide, a rhodium salt, a rhodium halide or a rhodium complex.

* * * * *